United States Patent
Johnson et al.

(10) Patent No.: US 9,701,596 B2
(45) Date of Patent: Jul. 11, 2017

(54) SYNTHESIS OF POLYCYCLIC AROMATIC HYDROCARBONS

(71) Applicant: The University of New Hampshire, Durham, NH (US)

(72) Inventors: Richard Peter Johnson, Newmarket, NH (US); Rajesh Thamatam, Durham, NH (US)

(73) Assignee: The University of New Hampshire, Durham, NH (US)

( * ) Notice: Subject to any disclaimer, the term of this patent is extended or adjusted under 35 U.S.C. 154(b) by 367 days.

(21) Appl. No.: 14/311,858

(22) Filed: Jun. 23, 2014

(65) Prior Publication Data
US 2014/0378727 A1     Dec. 25, 2014

Related U.S. Application Data

(60) Provisional application No. 61/839,167, filed on Jun. 25, 2013.

(51) Int. Cl.
*C07C 2/70* (2006.01)
*C07C 2/84* (2006.01)

(52) U.S. Cl.
CPC ............. *C07C 2/70* (2013.01); *C07C 2/84* (2013.01); *C07C 2103/54* (2013.01); *C07C 2531/02* (2013.01); *C07C 2531/025* (2013.01)

(58) Field of Classification Search
CPC .......... C07C 2/70; C07C 2/84; C07C 2103/54
See application file for complete search history.

(56) References Cited

U.S. PATENT DOCUMENTS 7,368,624 B2    5/2008    Brown et al.

OTHER PUBLICATIONS

Avlasevich, "Facile Synthesis of Terrylene and It's Isomer Benzoindenoperylene," J. Mater. Chem., 16, (2006), 1053-1057.
Li, "Bis-N-Annulated Quaterrylene: An Approach to Processable Graphene Nanoribbons," Org. Lett., vol. 11, No. 6, (2009).
Avlasevich, "Synethesis and Applications of Core-Enlarged Perylene Dyes," J. Mater. Chem., 20, (2010) 3814-3826.
Nagarajan, "Methylterrylene Isomers," Tetrahedron, 68, (2012), 9371-9375.

*Primary Examiner* — Sharon Pregler
*Assistant Examiner* — Alyssa L Cepluch
(74) *Attorney, Agent, or Firm* — Grossman, Tucker, Perreault & Pfleger, PLLC

(57) ABSTRACT

The present invention relates to the synthesis of polycyclic aromatic compounds. Compounds such as terrylene or quaterrylene may now be prepared in relatively high yield by reaction of naphthalene or perylene via Scholl-type coupling in the presence of a superacid and an oxidant in an inert solvent.

7 Claims, 2 Drawing Sheets n = 1 napthalene (1)
n = 2 perylene (2)
n = 3 terrylene (3)
n = 4 quaterrylene (4)

n = 1 napthalene (1)
n = 2 perylene (2)
n = 3 terrylene (3)
n = 4 quaterrylene (4)

SYNTHESIS OF POLYCYCLIC AROMATIC HYDROCARBONS

CROSS-REFERENCE To RELATED APPLICATIONS

This application claims the benefit of U.S. Provisional Application No. 61/839,167 filed Jun. 25, 2013.

FIELD OF THE INVENTION

The present invention relates to the synthesis of polycyclic aromatic hydrocarbons. For example, naphthalene may be converted to terrylene and perylene may be converted to quaterrylene. Relatively high yields of such products are now afforded by reaction of selected arene compound starting materials in the presence of a superacid and an oxidant.

BACKGROUND

As the smallest structural components of graphene nanoribbons, polyperinaphthalenes, commonly known as rylenes (see FIG. 1) and their derivatives are of intense current interest. Long-chain rylenes absorb a broad spectrum of light and may display electrical conductivity. If rylenes are to find application as electronic or photovoltaic components, their economical and large-scale synthesis is essential.

It is surprising that efficient and scalable synthetic routes to the parent structures terrylene (3) and quaterrylene (4) have not been described. See again, FIG. 1. These important hydrocarbons were first reported many years ago but the best current methods still follow classic Scholl conditions, which are suitable only for small scale reactions.

Reference to the Scholl reaction above is more specifically a reference to the heating naphthalene with solid $AlCl_3$ resulted in a relatively low yield of perylene (milligram quantities). This is a two-step process, with initial formation of 1,1-binaphthyl, followed by intramolecular cyclization. Similar dimerization of perylene to quaterrylene was reported. See, e.g., Aromatic Hydrocarbons. XLVII. Synthesis of Benzologs of Perylene and Bisanthene, Chem. Ber. 1949, 82 46-60; Catldo et al, On The Way to Graphene: The Bottom-Up Approach to Very Large PAHs Using the Scholl Reaction, *Fullerenes, Nanotubes, Carbon Nanostruct.* 2011, 19 (8), 713-725.

SUMMARY

A process for forming a product compound containing aryl-aryl bonds, comprising reacting an arene hydrocarbon containing two aromatic rings fused by sharing two adjacent carbon atoms, in the presence of an oxidant, superacid and an inert solvent, thereby providing a reaction solution, wherein the product compound precipitates from said solution. The yields may be in the range of 15-85%.

BRIEF DESCRIPTION OF THE DRAWINGS

The detailed description below may be better understood with reference to the accompanying figures which are provided for illustrative purposes and are not to be considered as limiting any aspect of the invention.

DETAILED DESCRIPTION

The present invention relates to the synthesis of polycyclic aromatic compounds. Compounds such as terrylene or quaterrlyene may now be prepared in relatively high yield by reaction of naphthalene or perylene via Scholl-type coupling in the presence of a superacid and an oxidant such as quinone or molecular oxygen in an inert solvent. For example, quaterrlyene may be prepared in relatively high yield by the reaction of an arene hydrocarbon, such as perylene, in the presence of a superacid and a quinone in an inert solvent. Similarly, terrylene may now be prepared in relatively high yields from naphthalene. This one step procedure for terrylene synthesis from a naphthalene is superior to previous multi-step routes.

The yields herein are contemplated to be at least 15% and fall in the range of 15-85%. Reference to a superacid may be understood as any acid with an acidity that is greater than that of 100% pure sulfuric acid. One preferred superacid for use herein includes triflic acid ($CF_3SO_3H$). The oxidant, quinone, may preferably include those organic compounds derived from aromatic compounds (benzene) that replace an even number of —CH= groups with carbonyl (—C=O) groups. Preferably, the quinone may include 2,3-dicholoro-5,6-dicyanoquinone (DDQ). In addition, one may use molecular oxygen as the oxidant in place of the quinone. The inert solvent may include, e.g., dichloromethane, dichoroethane (DCE) or chlorobenzene.

Figure 1:
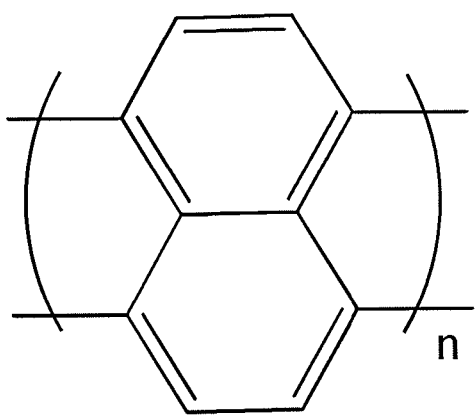
FIG. 1 Structures in the rylene series.

Reference to arene hydrocarbons is reference to fused and linked aromatic rings which may be further substituted. One particular class of arene hydrocarbons for which this invention is particular useful includes polycyclic aromatic hydrocarbons, such as naphthalene or perylene. As may be appreciated, both naphthalene or perylene, as starting compounds, include two aromatic rings that are fused by sharing two adjacent carbon atoms. See again, FIG. 1. Accordingly, naphthalene herein was converted to terrylene at yields of 30% and perylene was converted to quaterrylene at yields of 70% and perylene was converted to terrylene at yields of 17%. Accordingly, as noted, it is contemplated that the yields herein may fall in the range of 15% to 85%.

More specifically, the present invention is directed at a variation on the Scholl reaction (coupling of two arenes) employing a superacid catalyst in conjunction with 2,3-dichloro-5,6-dicyanoquinone (DDQ) to provide an efficient and easily scalable route to quaterrylene. The quaterrlyine structure herein was characterized by solution-phase NMR spectrum of its corresponding dication and by comparison of its ultraviolet/visible absorption spectrum with literature.

In preferred embodiment, the present invention is directed at refluxing dichloromethane (DCM) solutions of 2 with 2 equivalents of triflic acid ($CF_3SO_3H$) and 2 equivalents of DDQ to provde a dark green solid product which color is characteristic of quaterrylene structure. A minor product (5) is also believed to be formed as approximately 10% of the isolated solid. See Scheme 1 below:

SCHEME 1. Synthesis of Quaterrylene

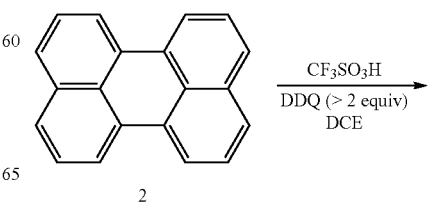

2

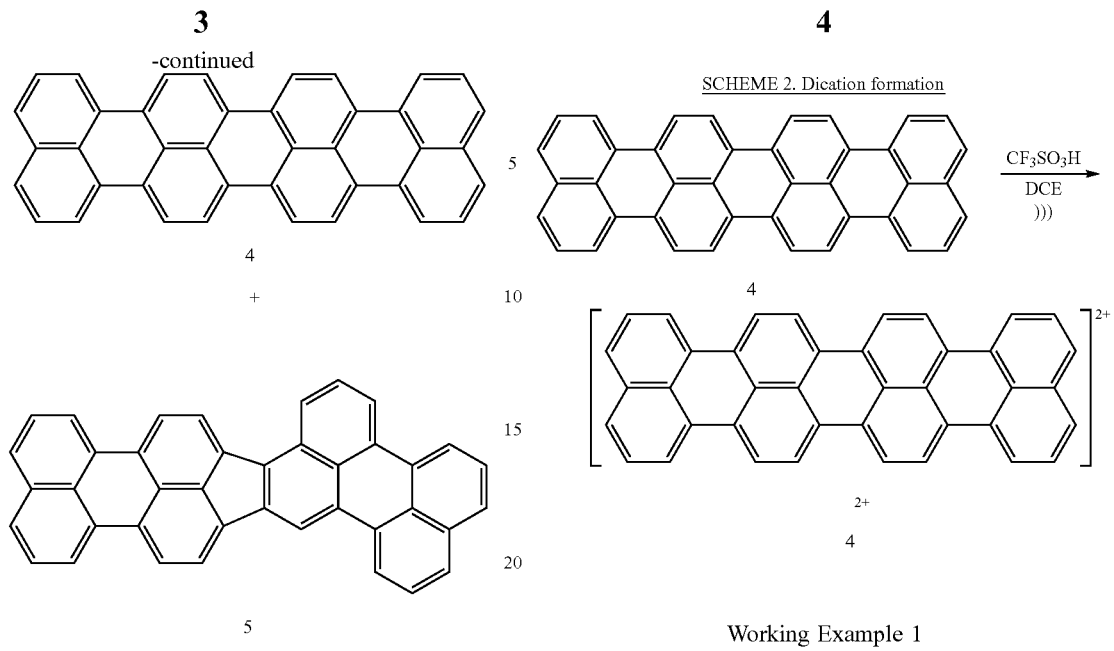

SCHEME 2. Dication formation

During the reaction, the product precipitates from solution. Neutralization of the cooled mixture with diisopropylethylamine, filtration, and washing the solid product with methanol gave a 96% crude yield. Successive Soxhlet extraction of the solid product with boiling methanol, toluene and chlorobenzene afforded a dark green nonfluorescent solid (83% yield from perylene). Following earlier precedent, this sample is expected to contain quaterrylene, but with isomer 5 as a minor component; this would result from a second mode of ring cyclization in the second step, perhaps preceded by rearrangement. The MALDI mass spectrum of this material is exceptionally simple, showing a peak with m/Z=500 ($C_{40}H_{20}$.) A smaller peak at m/Z=515 is attributed to oxygen addition to the mass spectral sample.

This sample was further characterized as quaterrylene by a novel NMR technique. The well-known insolubility of highly crystalline substances such as quaterrylene suggests that NMR spectral characterization should be impossible; however, many protonated arenes and arene oxidative dications (neutral minus two electrons) have been observed in solution and we investigated whether protonation might increase solubility and facilitate NMR analysis.

Figure 2:
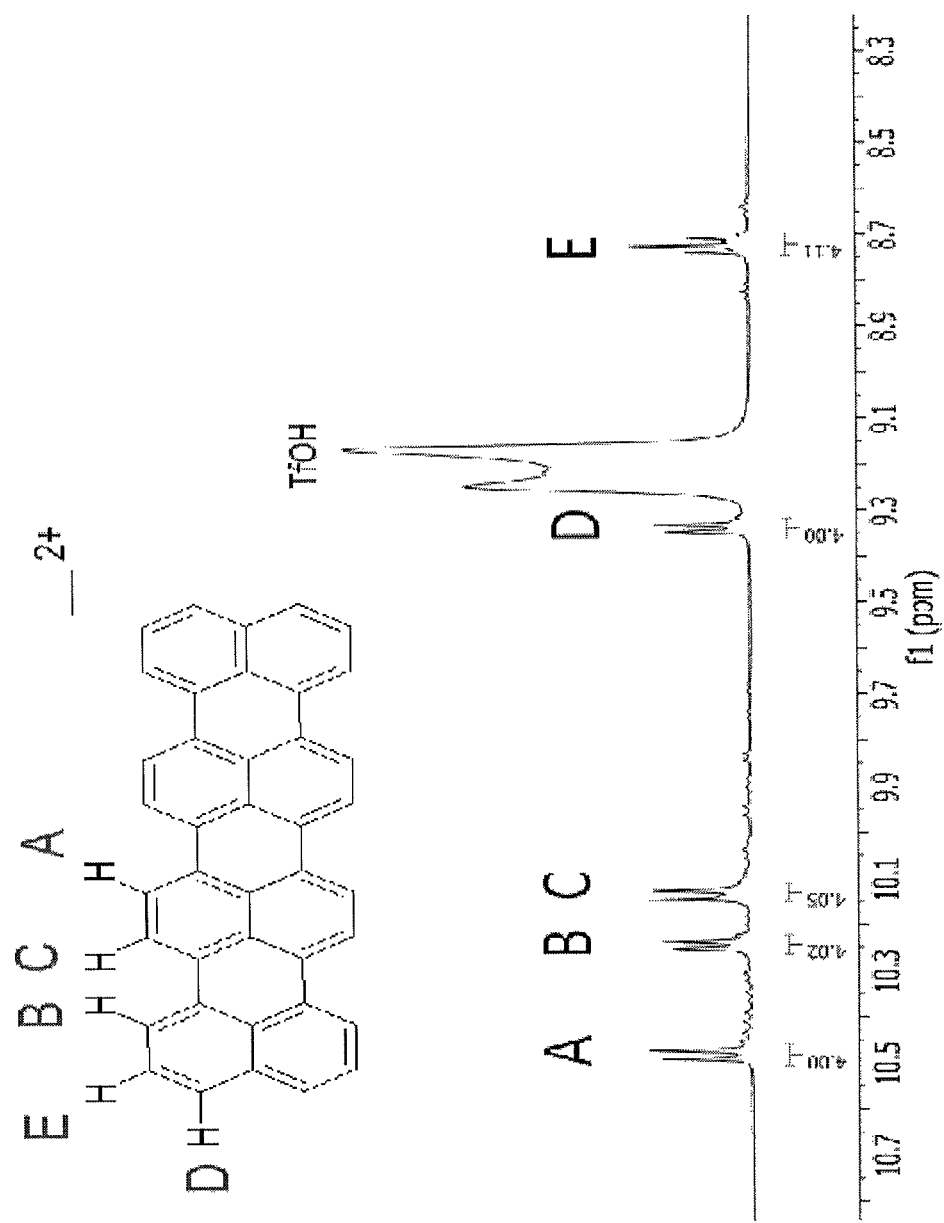
FIG. 2 $^1H$ NMR spectrum of quaterrylene dication $(C_{40}H_{20}^{2+})$.

Quaterrylene is insoluble in neutral dichloroethane (DCE), but with the aid of mild sonication, it was observed that small amounts of our sample, e.g. 10-20 mg/ml, dissolved readily in 1 M triflic acid-d/DCE-$d_4$, with formation of a dark bluish green solution. The $^1$H NMR spectrum of this sample (FIG. 2) showed five principle resonances, with peak integration and spin multiplicity expected for a symmetrical structure such as 4. Observed chemical shifts do not support a neutral structure but are in excellent agreement with GIAO B3LYP/6-31G* predicted chemical shifts for the dication ($C_{40}H_{20}^{2+}$, Scheme 2). Predicted shifts and expected multiplicities for the dication are: 8.75 (triplet), 9.17 (doublet), 9.78, (doublet), 9.85, (doublet), 10.06 (doublet). Minor resonances in the spectrum may correspond to the dication of 5 or to monoprotonated 4.

Working Example 1

Synthesis of Quaterrylene from Perylene. To a solution of perylene (1.00 g, 3.96 mmol) in dichloromethane (30 mL) was added triflic acid (1.75 ml, 19.8 mmol) over 5 min at room temperature. DDQ (1.80 g, 7.92 mmol) was added and the mixture was refluxed for 8 h under a nitrogen atmosphere. Progress of the reaction was monitored by TLC which showed a rapid loss of starting material. After cooling to ambient temperature, the reaction was quenched with a slight excess of diisopropylethylamine and diluted with methanol (30 ml). The resultant precipitate was filtered and washed with methanol and dichloromethane to give 0.96 g of dark green solid. Successive Soxhlet extraction (8 h each) with methanol, toluene and then chlorobenzene, followed by drying under vacuum, gave 0.83 g (83%) of dark green solid.

In addition to the above, the present invention also extends to the synthesis of terrylene from the reaction of naphthalene with a quinone, such as dichlorodicyanoquinone and a super acid (e.g. triflic acid). A working example is provided below.

Working Example 2

Synthesis of Terrylene from Naphthalene

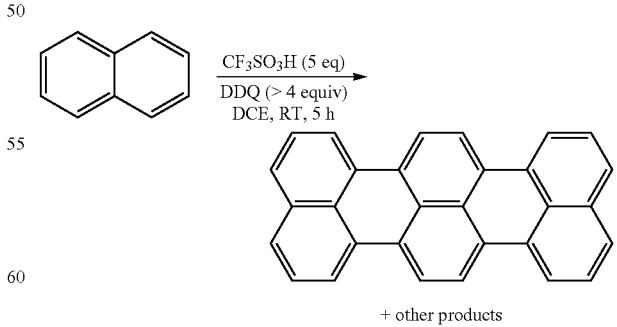

+ other products

Procedure 1: To a solution of naphthalene (1.00 g, 7.80 mmol) in dichloroethane (30 mL) was added triflic acid (3.40 ml, 39.0 mmol) and the mixture was stirred for 5 minutes at room temperature. DDQ (7.08 g, 31.20 mmol, 1 equivalent per C—C bond formation) was added, followed by stirring for 5 h under a nitrogen atmosphere. The progress of the reaction was monitored by TLC. After completion of the reaction, it was quenched with diisopropylethylamine at room temperature and diluted with methanol (30 ml). The resultant precipitate was filtered and washed with methanol and dichloromethane to give 0.67 g of dark violet solid. The solid was then transferred to a thimble and extracted in a Soxhlet apparatus first with dichloromethane (50 ml) for 24 h and later with toluene (50 ml) for 3 days. The toluene extract was cooled to room temperature and centrifuged to give 0.16 g of dark violet solid. Yield 17%. This substance was characterized as primarily terrylene by its UV/VIS (in N-methylpyrrolidone as solvent) and MALDI mass spectra.

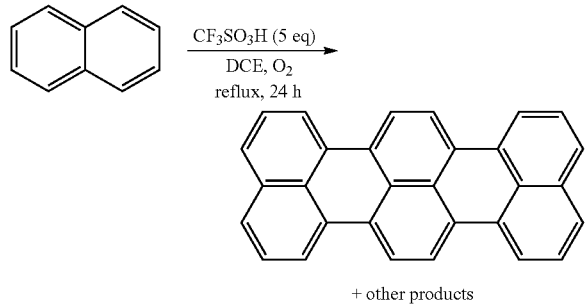

+ other products

Procedure 2. A solution of naphthalene (1.00 g, 7.80 mmol) in dichloroethane (30 mL) was degassed and purged with oxygen gas. Triflic acid (3.40 ml, 39.0 mmol) was then added and the mixture was refluxed for 24 h under an oxygen atmosphere. The progress of the reaction was monitored by TLC. After completion of the reaction, it was quenched with diisopropylethylamine at room temperature and diluted with methanol (30 ml). The resultant precipitate was filtered and washed with dichloromethane to give 0.73 g of dark purple solid. The solid was then transferred to a thimble and extracted in a Soxhlet apparatus, first with dichloromethane (50 ml) for 24 h and later with toluene (50 ml) for 3 days. The toluene extract was cooled to room temperature and centrifuged to give 0.27 g of dark violet solid. Yield 28%. This substance was characterized as primarily terrylene by its UV/VIS (in N-methylpyrrolidone as solvent) and MALDI mass spectra.

Working Example 3

Synthesis of Terrylene from Perylene

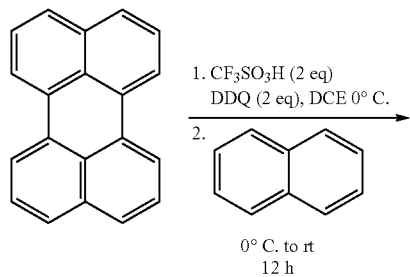

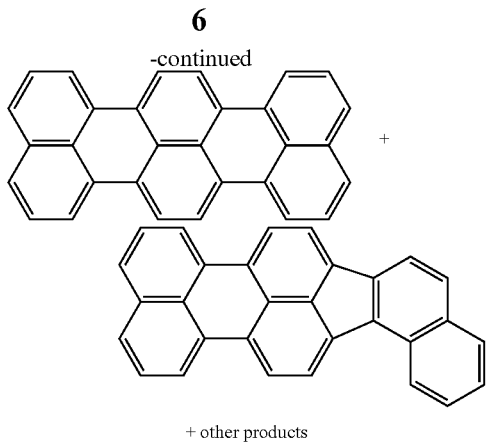

+ other products

To a solution of Perylene (1.00 g, 3.96 mmol) in dichloroethane (30 mL) at 0° C. was added triflic acid (0.7 ml, 7.93 mmol) and the mixture stirred for 5 minutes at room temperature. Then the mixture was treated with DDQ (1.8 g, 7.93 mmol, 1 equivalent per C—C bond formation) and stirred for 5 minutes under a nitrogen atmosphere. Naphthalene (0.53 g, 4.15 mmol) dissolved in dichloroethane (10 ml) was added slowly to the reaction mixture at 0° C. and the mixture was stirred for 2 hours at 0° C. before being warmed to room temperature. After stirring for 12 h at room temperature, the reaction was quenched with diisopropylethylamine and diluted with methanol (30 ml). The resultant precipitate was filtered and washed with methanol and dichloromethane to give 0.91 g of dark orange solid. The solid was then transferred to a thimble and extracted in a Soxhlet apparatus first with dichloromethane (50 ml) for 24 h and later with toluene (50 ml) for 2-3 days. The toluene extract was cooled to room temperature and centrifuged to give 0.46 g of dark violet solid. Yield 31%. This substance was characterized as primarily terrylene by its UV/VIS (in N-methylpyrrolidone as solvent) and MALDI mass spectra.

The mechanism of Scholl reactions has been the subject of much debate, with arguments made for both radical cation and arenium ion intermediates. The remarkable facility of dication formation from 4 provides clues to the relatively highly efficient coupling observed in the present invention. Perylene dications have been reported under stable ion conditions. This electrophilic species should couple easily with another molecule of neutral 2. The resulting 1,1'-biperylene can cyclize to 4 or rearrange by 1,2-shift to 1,2'-biperylene, which may then cyclize to the presumed minor isomer 5. Our results are consistent with the general observation that the efficiency of Scholl coupling increases with molecular size.

While there is much precedent for oxidative or acid-catalyzed arene coupling and polymerization, the high efficiency of the present coupling and cyclization reaction appears to result from a combination of superacid catalyst, stoichiometric equivalency of DDQ relative to the number of new sigma bonds, and insolubility of the final product in the reaction medium. It is also preferred that reactants and intermediate structures are soluble in this medium so the reaction can proceed to completion, while the insolubility of product prevents further reaction. A dication mechanism may be operative. The technique herein therefore provides an efficient route to quaterrylene.

What is claimed is:

1. A process for forming a product compound containing an aryl-aryl bond, comprising reacting an arene hydrocarbon containing two aromatic rings fused by sharing two adjacent carbon atoms, in the presence of an oxidant, superacid and an inert solvent, thereby providing a reaction solution, wherein the product compound precipitates from said solution, wherein said oxidant comprises molecular oxygen.

2. The process of claim 1 wherein said arene compound comprises naphthalene and said product compound comprises terrylene.

3. The process of claim 1 wherein said arene compound comprises perylene and said product compound comprises quaterrylene.

4. The process of claim 1 wherein said arene compound comprises perylene and said product compound comprises terrylene.

5. The process of claim 1 wherein said product compound is recovered at a yield of 15-85%.

6. The process of claim 1 wherein said superacid comprises triflic acid.

7. The process of claim 1 wherein said inert solvent comprises dichloromethane, dichlorethane or chlorobenzene.

* * * * *